DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED NOVEMBER 21, 1972

904 O.G. 274

T904,021

PREPARATION OF DIOLS FROM UNSATURATED ALCOHOLS

Harry B. Copelin, Wilmington, Del., assignor to E. I. du Pont de Nemours and Company, Wilmington, Del.

Filed July 26, 1971, Ser. No. 166,315

Int. Cl. C07c *31/18, 47/18*

U.S. Cl. 260—635 A

No Drawing. 9 Pages Specification

The invention relates to a process for the production of diols by the hydroformylation of unsaturated alcohols and hydrogenation of the hydroformylated product in an aqueous media. The process requires the use of phosphine complexes of rhodium to produce the desired high yields of diols. Most of the diols so produced are valuable components in the production of polyethers and polyesters.